(12) United States Patent
Shan

(10) Patent No.: US 12,082,816 B2
(45) Date of Patent: Sep. 10, 2024

(54) CLOSURE DRIVING MECHANISM AND SURGICAL STAPLER

(71) Applicant: Touchstone International Medical Science Co., Ltd., Suzhou (CN)

(72) Inventor: Teng Shan, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 240 days.

(21) Appl. No.: 17/634,780

(22) PCT Filed: Aug. 27, 2020

(86) PCT No.: PCT/CN2020/111791
§ 371 (c)(1),
(2) Date: Feb. 11, 2022

(87) PCT Pub. No.: WO2021/037153
PCT Pub. Date: Mar. 4, 2021

(65) Prior Publication Data
US 2022/0323077 A1    Oct. 13, 2022

(30) Foreign Application Priority Data

Aug. 29, 2019 (CN) .......................... 201910806837.8
Aug. 29, 2019 (CN) .......................... 201921425349.4

(51) Int. Cl.
*A61B 17/115* (2006.01)
(52) U.S. Cl.
CPC .................................. *A61B 17/115* (2013.01)
(58) Field of Classification Search
CPC ........................... A61B 17/068; A61B 17/115
See application file for complete search history.

(56) References Cited

U.S. PATENT DOCUMENTS 5,307,976 A * 5/1994 Olson .............. A61B 17/07207
227/175.3
2007/0194081 A1 8/2007 Hueil et al.
(Continued)

FOREIGN PATENT DOCUMENTS

CA            3072771 A1    2/2019
CN         101317780 A     12/2008
(Continued)

OTHER PUBLICATIONS

English Translation of International Search Report issued for International Patent Application No. PCT/CN2020/111791 on Mar. 4, 2021 (2 pages).
(Continued)

*Primary Examiner* — Robert F Long
*Assistant Examiner* — Xavier A Madison
(74) *Attorney, Agent, or Firm* — Fox Rothschild LLP

(57) ABSTRACT

A closure driving mechanism and a surgical stapler are provided. The closure driving mechanism includes a firing handle, a first slider, a locking member, a closure driver, and an actuating rod. The locking member fits with the first slider when the firing handle is actuated in an initial state and separates from the first slider after the stapler being fired. Therefore, the closure driver is locked by the fit cooperation between the first slider and the locking member after a head assembly is closed, to avoid the pulling sheet from moving distally during a firing process. After the firing process is fired, the locking member no longer locks the closure driver, therefore, the cartridge and the anvil can be opened automatically.

14 Claims, 16 Drawing Sheets

(56) References Cited

U.S. PATENT DOCUMENTS

| | | |
|---|---|---|
| 2010/0264194 A1 | 10/2010 | Huang et al. |
| 2015/0136833 A1 | 5/2015 | Shelton, IV et al. |
| 2018/0110516 A1 | 4/2018 | Baxter, III et al. |
| 2019/0000467 A1 | 1/2019 | Shelton, IV et al. |

FOREIGN PATENT DOCUMENTS

| | | |
|---|---|---|
| CN | 101327139 A | 12/2008 |
| CN | 102743203 A | 10/2012 |
| CN | 106419983 A | 2/2017 |
| CN | 210990512 U | 7/2020 |
| EP | 3123956 A2 | 2/2017 |
| JP | H09164144 A | 6/1997 |
| JP | 2008212672 A | 9/2008 |
| JP | 2011224375 A | 11/2011 |
| JP | 2014531262 A | 11/2014 |

OTHER PUBLICATIONS

Extended European Search Report issued on Sep. 29, 2022 for European Patent Application No. 20856206.6 (6 pages).
Japanese Decision to Grant a Patent issued on Apr. 21, 2023 for Japanese Patent Application No. 2022-512355 (3 pages).

\* cited by examiner

CLOSURE DRIVING MECHANISM AND SURGICAL STAPLER

CROSS-REFERENCE TO RELATED APPLICATIONS

This application is based upon PCT patent application No. PCT/CN2020/111791, filed on Aug. 27, 2020, which claims priority to Chinese Patent Applications No. 201910806837.8, and No. 201921425349.4, filed on Aug. 29, 2019, the entire contents of which are incorporated herein by reference.

TECHNICAL FIELD

The present disclosure relates to medical instruments' technology, more particularly, to a closure driving mechanism and a surgical stapler.

BACKGROUND

Digestive tract disease is one of human diseases of high incidence. During treatment, a surgical stapler is widely used for suturing physiological tissues such as tissues in the digestive tract, instead of the manual operation by doctors. The surgical stapler is a common surgical instrument, and used for end-to-end anastomosis, or end-to-side anastomosis of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the surgical stapler includes an instrument body, a firing handle rotatably connected to the instrument body and a head assembly cooperated with the instrument body. The head assembly includes a cartridge and an anvil located relative to each other. During the operation, the firing handle is actuated for a first time, a pulling sheet of the head assembly is pulled by a closure driving mechanism to move proximally, to close the cartridge and the anvil. After the head assembly is closed, the firing handle is actuated again, the staples are pushed towards the tissues and form a closed shape at the anvil to suture the tissues. Meanwhile, a cutter moves distally to cut the tissues. In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site.

The traditional closure driving mechanism has a complex structure. Furthermore, the pulling sheet may move distally, affecting the closure effect between the cartridge and the anvil, thereby affecting the surgical effect. Furthermore, after the stapler including the traditional closure driving mechanism is fired, the cartridge and the anvil are still closed, in addition to the normal operation, the operator still needs to operate to open the cartridge and the anvil. Furthermore, after the stapler being fired, the operator needs to pull a cutter pushing rod back, to drive the cutter to move back to its initial position along a cutter groove. If the cartridge and the anvil are still closed during the pulling-back process of the cutter, the cutter cannot return to its initial position smoothly due to the resistance from the tissues between the cartridge and the anvil.

SUMMARY

To solve the problems in the prior art, the present disclosure provides a closure driving mechanism and a surgical stapler, wherein the position of a closure driver is locked by fitting cooperation between a locking member and a first slider when the head assembly is closed, thereby avoiding the pulling sheet moving distally during the firing process, after the stapler being fired, the closure driver is no longer locked by the locking member, then the cartridge and the anvil can be automatically opened.

In the present disclosure, a closure driving mechanism used for a surgical stapler having a head assembly, wherein the mechanism comprises a firing handle, a first slider, a locking member, a closure driver, and an actuating rod, wherein, the actuating rod is provided with a pressing portion and an avoiding portion; in an initial state, the pressing portion, the avoiding portion and at least a part of the first slider are all located at a proximal side of the locking member;

when the firing handle is actuated in the initial state, the first slider is moved distally by the firing handle until the first slider is under the locking member, thereby moving the closure driver to close the head assembly, the pressing portion moves distally and presses the locking member downwards to fit with the first slider;

after the stapler being fired, the avoiding portion is moved to be above the locking member, allowing the locking member to move upwards and at least partially enter the avoiding portion, to separate from the first slider.

In some embodiments, an upper surface of the first slider is provided with a groove, in the initial state, the groove is located at the proximal side of the locking member; when the firing handle is actuated in the initial state, at least a part of the locking member enters the groove of the locking member; or the locking member is provided with a groove recessed upwards, when the firing handle is actuated in the initial state, at least a part of the first slider enters the groove of the locking member.

In some embodiments, the pressing portion is a ledge located on a distal side of the actuating rod, and the avoiding portion is recessed upwards relative to the ledge.

In some embodiments, a distal side surface of the ledge is a first inclined surface of the ledge which is inclined upwards from a proximal side to a distal side thereof, a proximal side surface of the locking member is a first inclined surface of the locking member which cooperates with the first inclined surface of the ledge.

In some embodiments, the avoiding portion is an avoiding groove formed on the ledge.

In some embodiments, a distal side surface of the avoiding groove is a second inclined surface of the ledge which is inclined upwards from a distal side to a proximal side thereof, a distal side surface of the locking member is a second inclined surface of the locking member which cooperates with the second inclined surface of the ledge.

In some embodiments, the avoiding portion is located between a proximal side of the ledge and the actuating rod.

In some embodiments, a proximal side surface of the ledge is a second inclined surface of the ledge which is inclined upwards from a distal side to a proximal side thereof, a distal side surface of the locking member is a second inclined surface of the locking member which cooperates with the second inclined surface of the ledge.

In some embodiments, an upper surface of the first slider is provided with a groove, the locking member includes a second slider and a third slider, the third slider is provided with an accommodating groove housing the second slider, and a boss is provided on a side of the second slider;

wherein, when the firing handle is actuated in the initial state, the boss of the second slider moves downwards and at least partially enters the groove of the first slider.

In some embodiments, a first biasing member is provided under the third slider, and applies an upward biasing force to the third slider.

In some embodiments, an upper surface of the first slider is provided with a groove, the locking member includes an elastic sheet having a movable end and a fixed end at a distal side of the movable end, the movable end is provided with a cooperation portion cooperated with the groove of the first slider, at least a part of the cooperation portion enters the groove of the first slider when the pressing portion presses the elastic sheet.

The present disclosure further provides a surgical stapler including the above closure driving mechanism.

The closure driving mechanism and the surgical stapler have the following advantages.

The present disclosure provides a closure driving mechanism for a surgical stapler. Before the stapler is fired, and after the head assembly is closed by a closure driver, the position of the closure driver is locked by fitting cooperation between the locking member and the first slider, thereby avoiding the pulling sheet moving distally during the firing process. After the stapler being fired, the locking member moves upwards to get out of the first slider, and no longer locks the position of the closure driver, the closure driver can return to its initial position, to open the cartridge and the anvil automatically. The operation steps are simplified for the operator and the cutter can be pulled back smoothly.

BRIEF DESCRIPTION OF THE DRAWINGS

Embodiments of the present disclosure will now be described, by way of example only, with reference to the accompanying schematic drawings. Apparently, the following figures are only exemplary. For the skilled in the art, other figures can also be gotten according to the following figures without creative work.

DETAILED DESCRIPTION

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

To solve the technical problem of the existing technology, the present disclosure provides a closure driving mechanism used for a surgical stapler and a surgical staple including the closure driving mechanism. The stapler includes a head assembly and an instrument body, and a pulling sheet is provided in the instrument body for closing the head assembly. The mechanism includes a firing handle, a first slider, a locking member, a closure driver, and an actuating rod. The actuating rod is provided with a pressing portion and an avoiding portion, in an initial state, at least a part of the first slider, the pressing portion and the avoiding portion are all located at a proximal side of the locking member. When the firing handle is actuated in the initial state, the first slider is moved by the firing handle distally until the first slider is under the locking member, thereby moving the closure driver to close the head assembly, the pressing portion moves distally and presses the locking member downwards to fit with the first slider. Therefore, the first slider is locked and cannot move proximally, and the pulling sheet won't move distally during the firing process of the stapler, to improve the closure stability of the head assembly.

After the stapler being fired, the avoiding portion is moved distally to be above the locking member, allowing the locking member to move upwards and at least partially enter the avoiding portion, to separate from the first slider. Therefore, the closure driver won't be locked by the locking component and the first slider and can return to its initial position. The pulling sheet is moved distally to open the cartridge and the anvil automatically. The operation steps of the stapler for the doctors are simplified, and the cutter can be pulled back smoothly.

The present disclosure further provides a surgical stapler including the closure driving mechanism. The closure stability of the head assembly during the firing process is improved, and the head assembly can be automatically opened after the stapler being fired.

Figure 15:
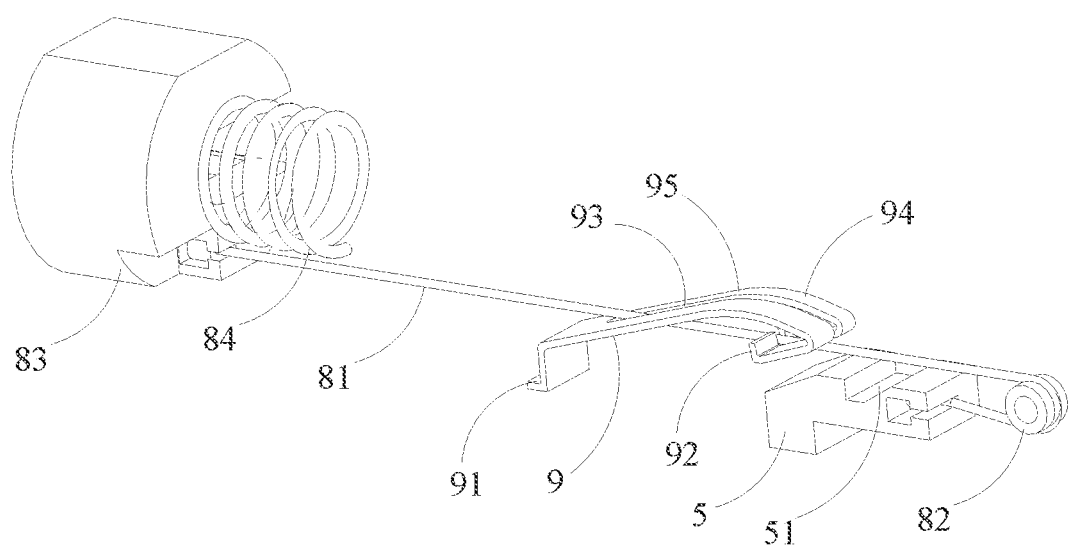
FIG. 15 is a structural schematic view of a closure driving mechanism according to a second embodiment of the present disclosure.
Figure 16:
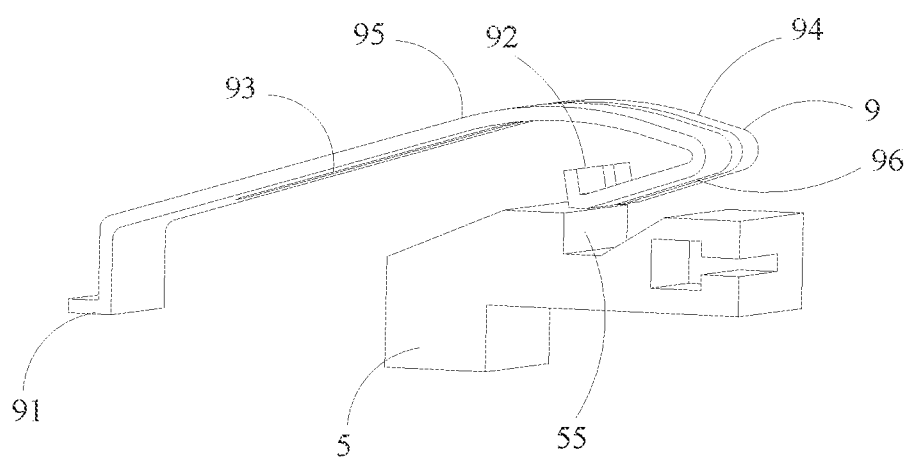
FIG. 16 is a structural schematic view of the positions of a first slider and a locking member according to a second embodiment of the present disclosure.

In the following, the structures of the closure driving mechanism and the stapler in specific embodiments are described combining FIGS. 1-16. FIGS. 1-14 show the structures of the closure driving mechanism and the stapler according to a first embodiment of the present disclosure. FIGS. 15 and 16 show the structures of the closure driving mechanism and the stapler according to a second embodiment of the present disclosure. Wherein, the locking member has different structures in the first embodiment and the second embodiment. It should be understood that the specific structures of the two embodiments are only exemplary, and are not intended to be a limitation to the protection scope of the present disclosure.

As shown in FIGS. 1-14, in the first embodiment of the present disclosure, the stapler includes an instrument body 1 and a head assembly (not shown in the drawings) located at a distal side of the instrument body 1. The instrument body 1 includes a housing 13 and a fixed handle 11, and further includes a pulling sheet 12 located therein. The pulling sheet 12 is used for closing and opening the head assembly. The head assembly is opened when the pulling sheet is in an initial state, and the head assembly is closed when the pulling sheet 12 moves proximally. Then the head assembly can be opened again when the pulling sheet 12 moves distally after the head assembly is closed. The closure driving mechanism includes a firing assembly 3, a first slider 5, a locking member, a closure driver 83 and an actuating rod 2. The closure driver 83 is connected to the pulling sheet 12. When the closure driver 83 moves proximally, the pulling sheet 12 is moved proximally to close the head assembly of the stapler.

Figure 1:
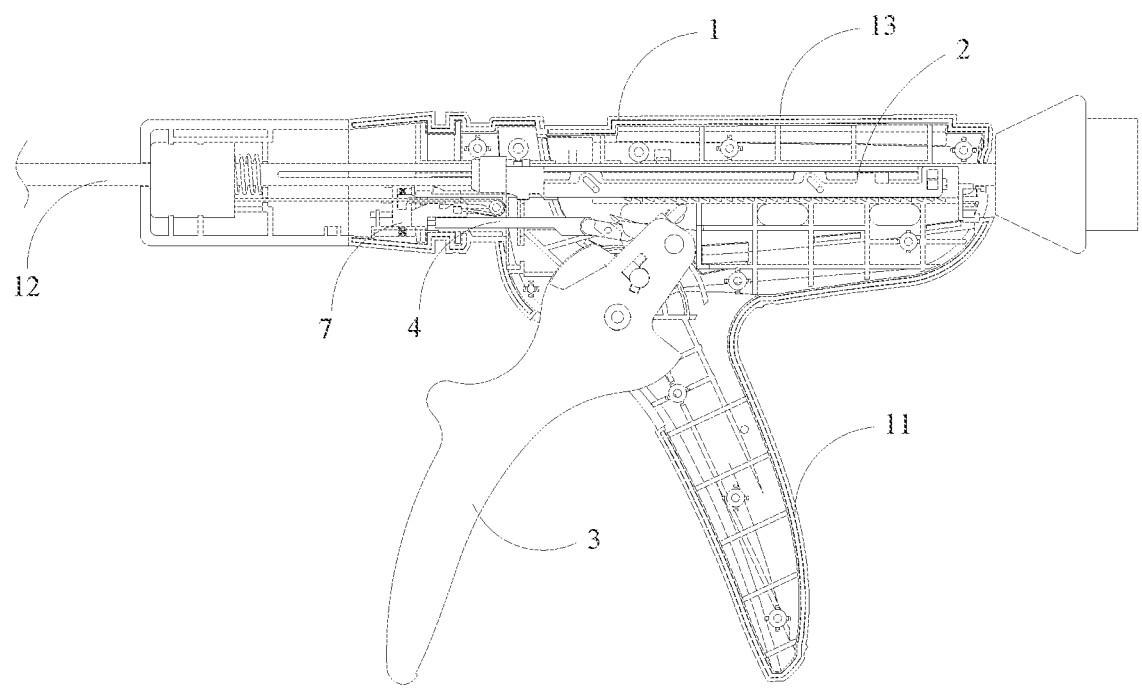
FIG. 1 is a structural schematic view of a part of a stapler in an initial state according to a first embodiment of the present disclosure.
Figure 2:
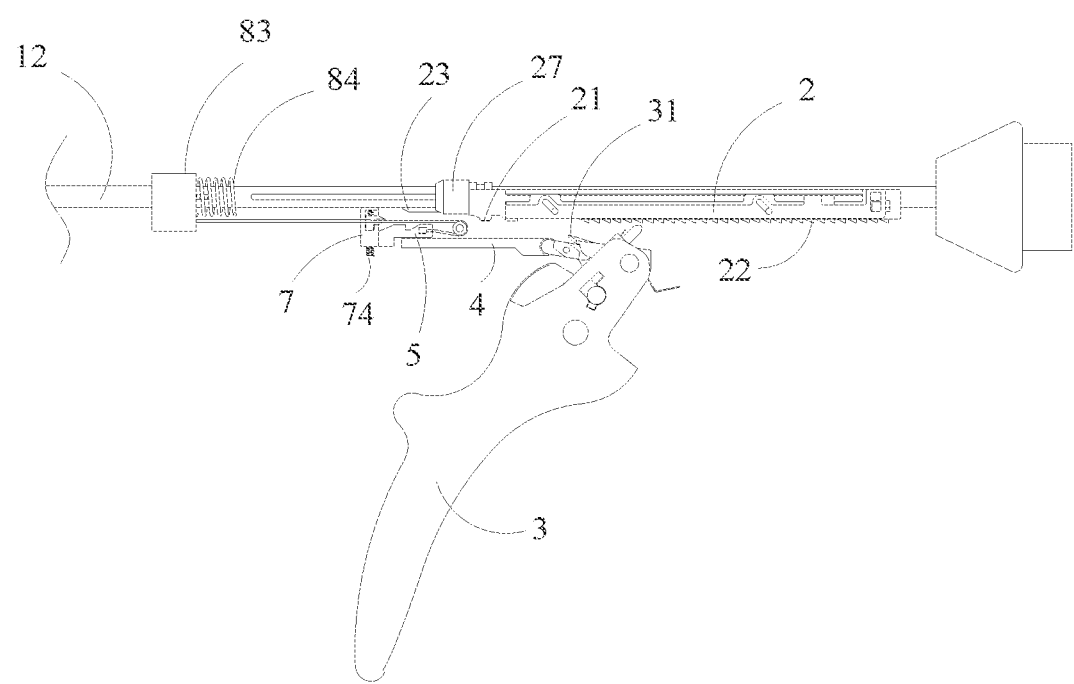
FIG. 2 is a structural schematic view of the stapler of FIG. 1 after a housing is removed.
Figure 3:
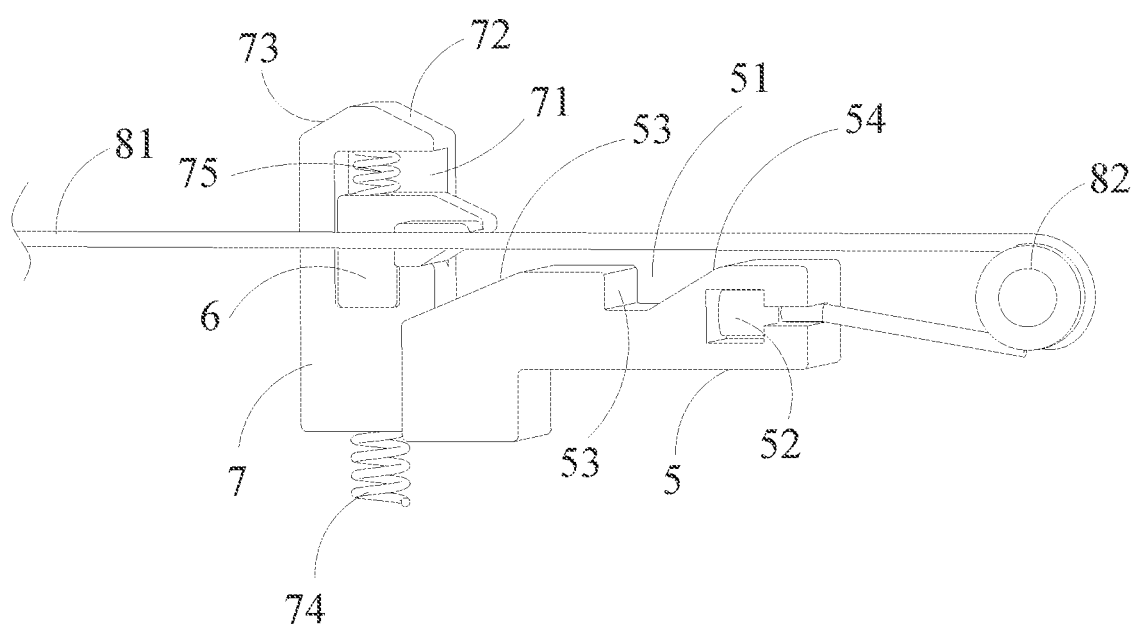
FIG. 3 is a schematic view of the positions of a first slider and a locking member in the initial state according to the first embodiment of the present disclosure.
Figure 4:
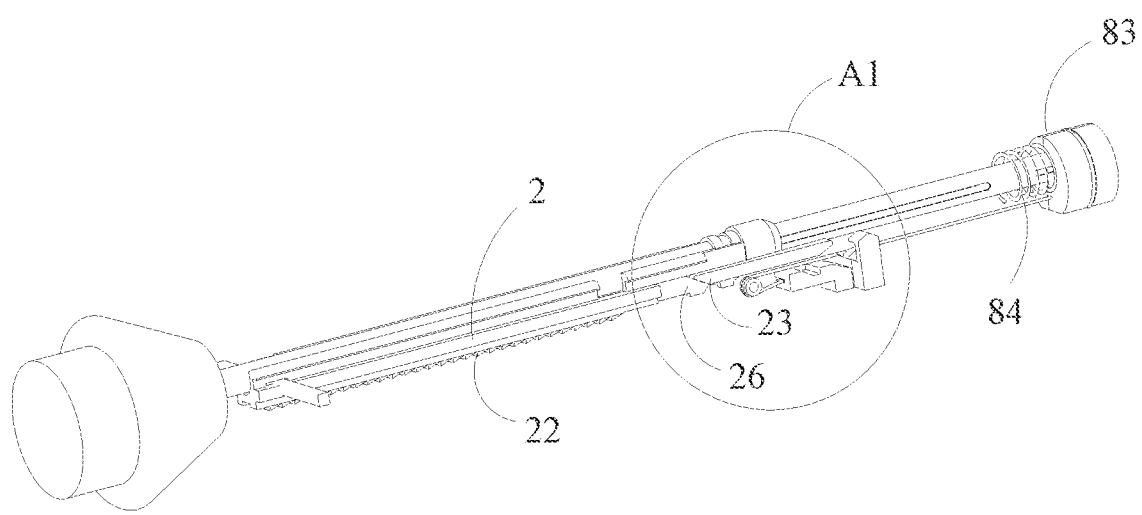
FIG. 4 is a structural schematic view of a closure driving mechanism in the initial state according to the first embodiment of the present disclosure.
Figure 5:
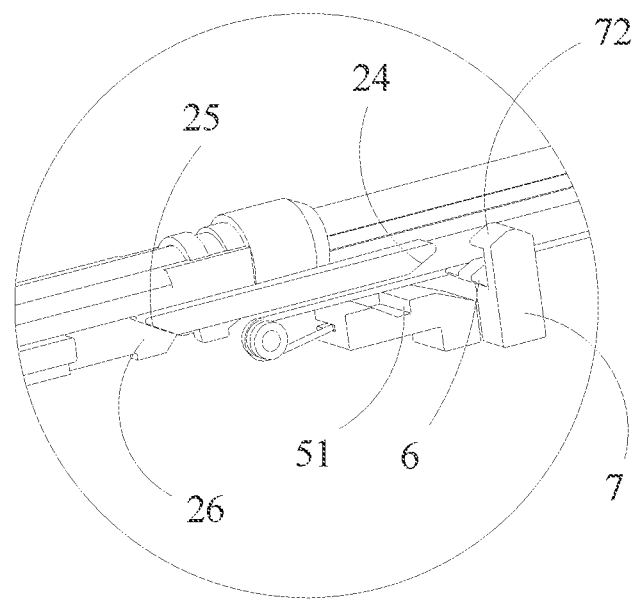
FIG. 5 is an enlarged view of A1 in FIG. 4.
Figure 6:
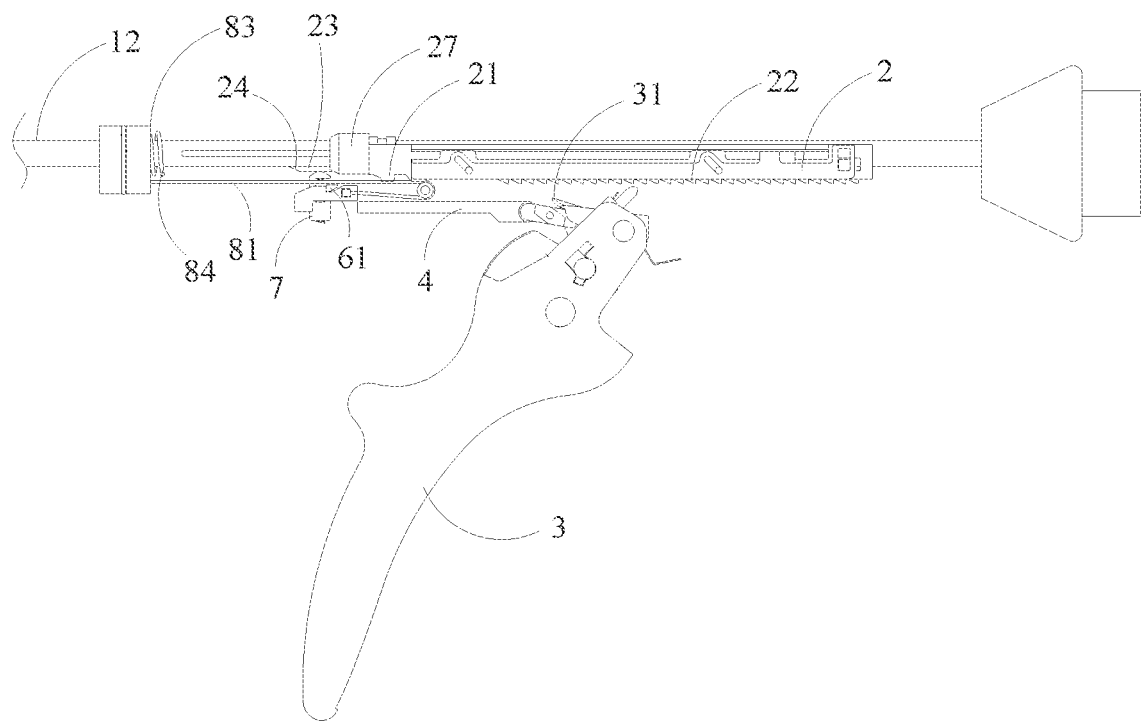
FIG. 6 is a structural schematic view of a part of the stapler after a firing handle is actuated for a first time in the initial state according to the first embodiment of the present disclosure.
Figure 7:
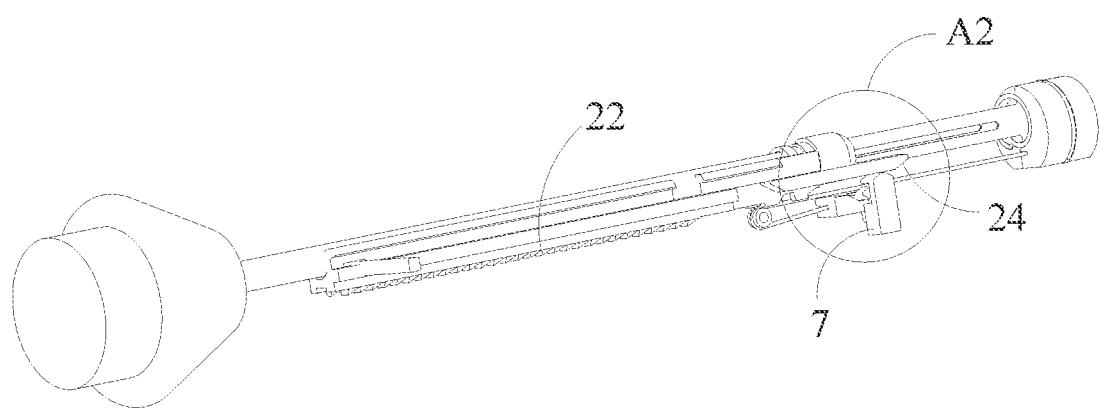
FIG. 7 is a structural schematic view of the closure driving mechanism after the firing handle is actuated for a first time in the initial state according to the first embodiment of the present disclosure.

FIGS. 1-5 show the structure of the closure driving mechanism in an initial state according to the first embodiment. In the initial state, the first slider 5 and the actuating rod 2 are both located in the initial positions thereof, the initial position of the first slider 5 is located at a proximal side of the locking member 60. The actuating rod 2 has a pressing portion 230 and an initial position of the pressing portion 230 is located at a proximal side of the locking member 60. As shown in FIG. 3, the locking member 60 includes a second slider 6 and a third slider 7. The third slider 7 is provided with an accommodating groove 71 housing the second slider 6. As shown in FIGS. 4 and 5, the pressing portion 230 of the actuating rod 2 is a ledge 23 provided on a distal side of the actuating rod 2.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site. The term "move distally" refers to moving towards a distal side of the stapler, and the term "move proximally" refers to moving towards a proximal side of the stapler. The terms "up", "upwards", "down" and "downwards" are used herein with reference to the actuating rod 2, wherein, the term "upwards" refers to a direction away from the gear 22, and the term "downwards" refers to a direction opposite to "upwards". For example, as shown in FIGS. 1 and 2, the distal side of the instrument body 1 is a left side thereof, the proximal side of the instrument body 1 is a right side thereof, the upward direction is a direction from a bottom end towards an up end. In FIG. 4, the perspective view is flipped from left to right relative to FIGS. 1 and 2, the distal side of the actuating rod 2 is a right side of the actuating rod 2, and the proximal side of the actuating rod 2 is a left side of the actuating rod 2.

When the firing handle 3 is actuated in the initial state, the rotation of the firing handle 3 results in a distal movement of a connecting rod 4, then the connecting rod 4 pushes the first slider 5 to move distally to be under the locking member. The first slider 5 is connected to the closure driver 83 through a turning assembly 80, which transforms the distal movement of the first slider 5 to a proximal movement of the closure driver 83. Therefore, the closure driver 83 drives the pulling sheet 12 to move proximally to close the head assembly of the stapler.

In the embodiment, the turning assembly 80 includes a support member fixed to the housing 13 and a rope 81. In a preferable embodiment, the support member is a pulley 82 to decrease a resistance to the rope 81 when the rope 81 is moving. The pulley 82 is located at a proximal side of the first slider 5, the rope 81 is arranged outside the pulley 82, and the rope 81 is connected between the first slider 5 and the closure driver 83. In a preferable embodiment, each of two ends of the rope 81 is provided with a fixed end. The proximal side of the first slider 5 is provided with a second groove 52, in which one fixed end of the rope 81 is removably mounted. The other fixed end of the rope 81 is removably connected to the closure driver 83. With the structures of the rope 81 and the pulley 82, the movement of the first slider 5 results in a driving force in a reverse direction to move the closure driver 83 proximally.

Simultaneously, when the firing handle 3 is actuated to rotate in the initial state, a claw 31 on the firing handle 3 contacts and drives a pushing tooth 21 on the actuating rod 2 to move distally, thereby moving the actuating rod 2 distally. The pressing portion of the actuating rod 2 moves distally to contact and press the locking member downwards, the locking member fits with the first slider 5 to avoid the first slider 5 moving proximally, so that the closure stability of the head assembly is improved.

FIGS. 6-10 show the structures of the stapler and the closure driving mechanism after the firing handle 3 is actuated for a first time. In the first embodiment, an upper surface of the first slider 5 is provided with a first groove 51, at least a part of the locking member enters the first groove 51 when the firing handle 3 is actuated in the initial state, to realize the fit cooperation between the first slider 5 and the locking member. In alternative embodiments, the fit cooperation between the locking member and the first slider 5 can also be realized by providing a groove recessed upwards on the locking member, then at least a part of the first slider 5 enters the groove of the locking member when the firing handle 3 is actuated in the initial state.

Figure 8:
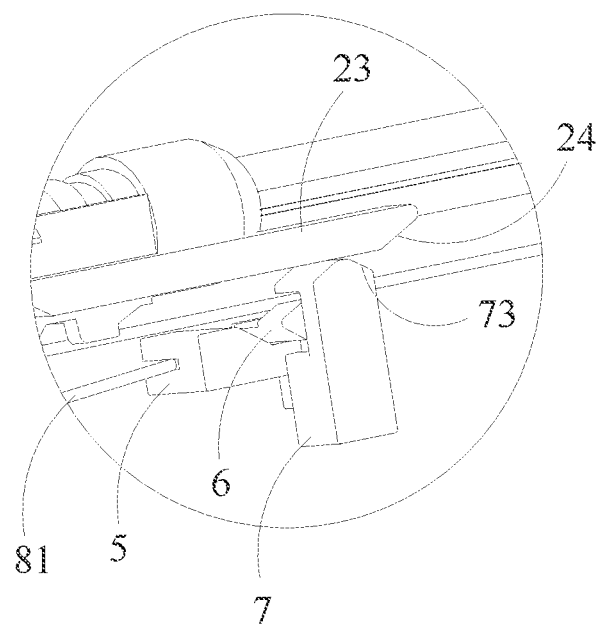
FIG. 8 is an enlarged view of A2 in FIG. 7.
Figure 9:
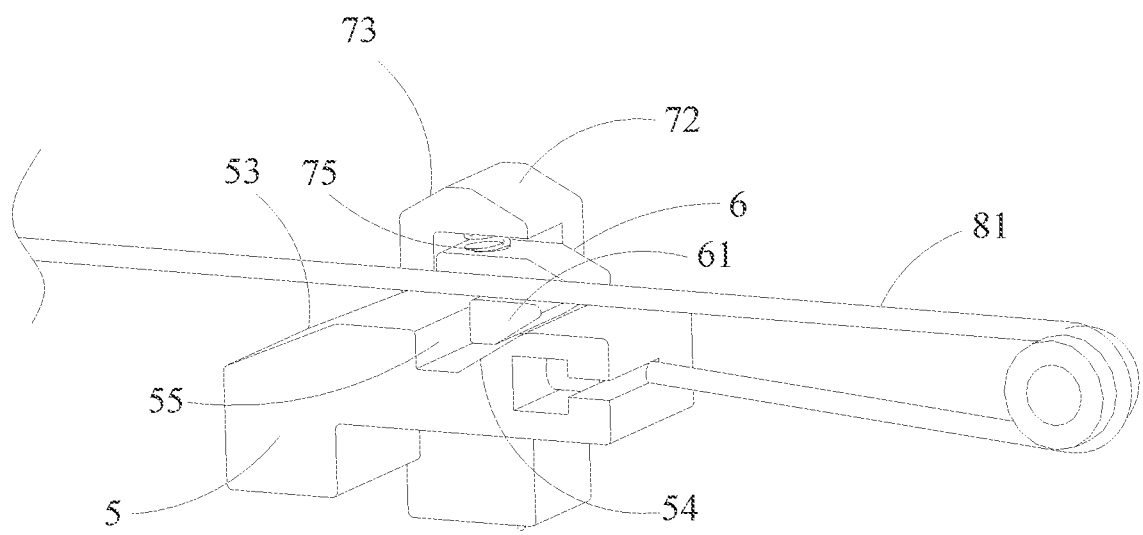
FIG. 9 is a schematic view of cooperation between the first slider and the locking member after the firing handle is actuated for the first time in the initial state according to the first embodiment of the present disclosure.
Figure 10:
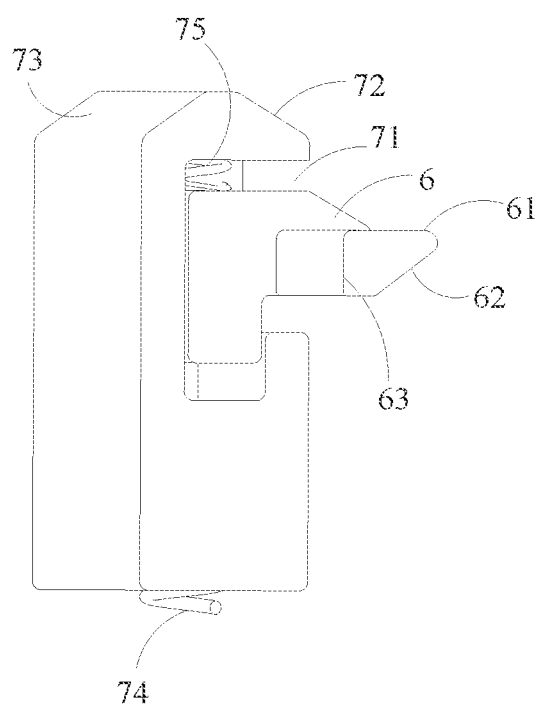
FIG. 10 is a structural schematic view of the locking member according to the first embodiment of the present disclosure.
Figure 11:
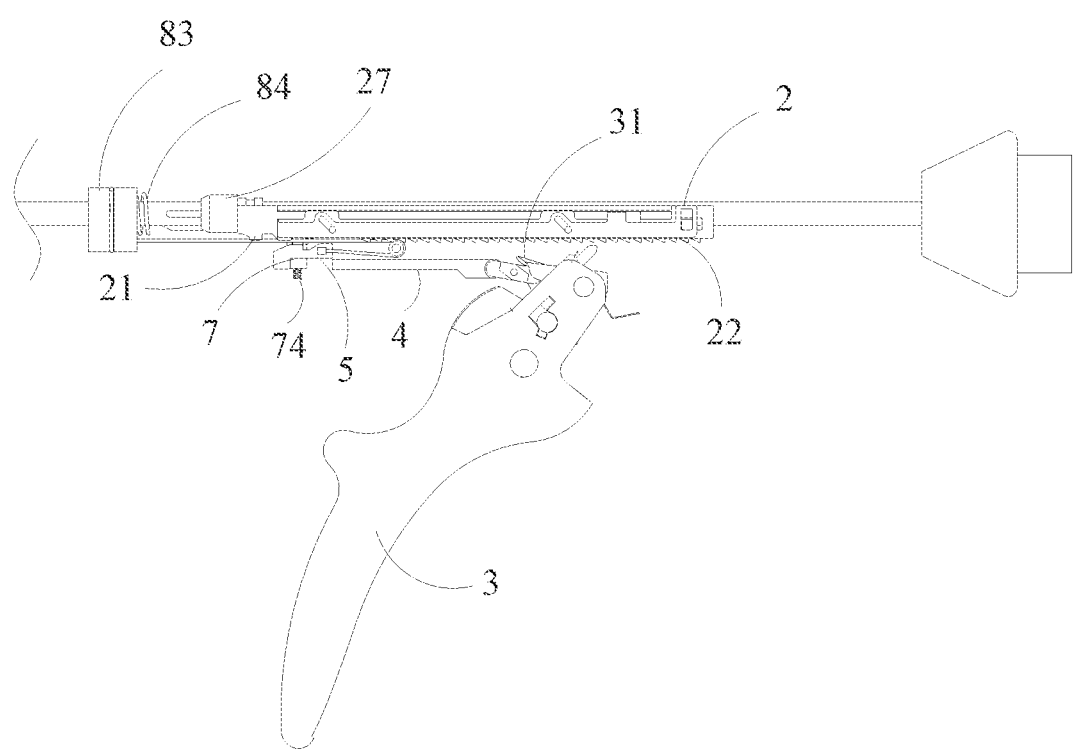
FIG. 11 is a structural schematic view of a part of the stapler after the stapler being fired according to the first embodiment of the present disclosure.
Figure 12:
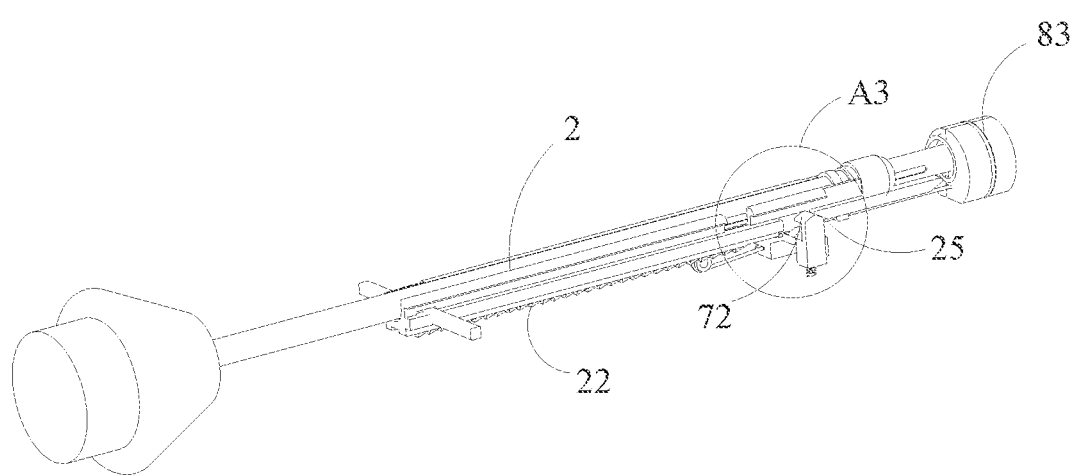
FIG. 12 is a structural schematic view of the closure driving mechanism after the stapler being fired according to the first embodiment of the present disclosure.
Figure 13:
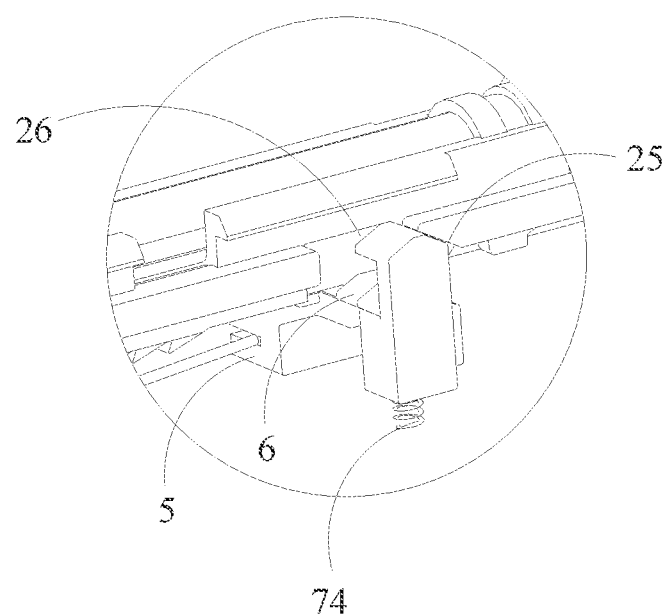
FIG. 13 is an enlarged view of A3 in FIG. 12.
Figure 14:
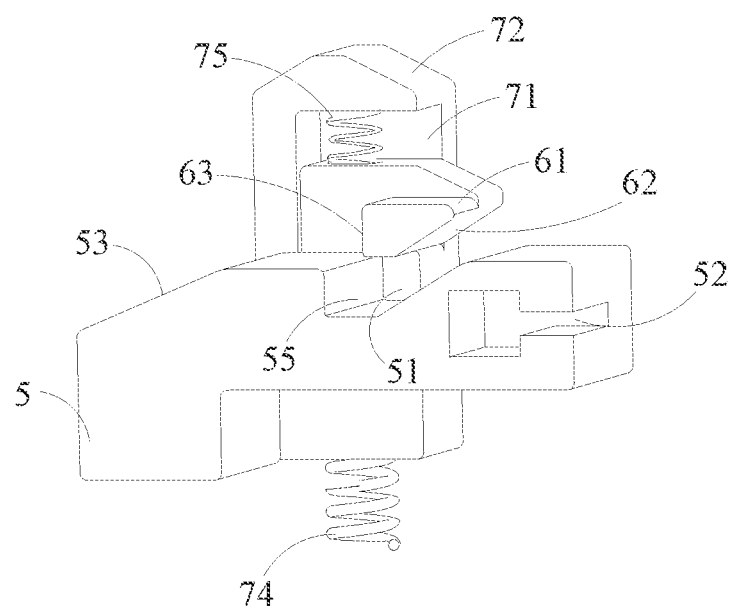
FIG. 14 is a structural schematic view of the positions of the first slider and the locking member after the stapler being fired according to the first embodiment of the present disclosure.

As shown in FIGS. 8-10, a boss 61 is provided on a side of the second slider 6. When the boss 61 is in its initial position, the boss 61 is located at a proximal side of the first groove 51, and the boss 61 is higher than the first groove 51. When the firing handle 3 is actuated in the initial state, the first slider 5 is moved distally to move the first groove 51 of the first slider 5 to be under the boss 61, and the ledge 23 moves distally to contact and presses the third slider 7 downwards. Under the pressure from the ledge 23, the third slider 7 drives the second slider 6 to integrally move downwards, so that the boss 61 of the second slider 6 moves downwards and at least a part of the second slider 6 enters the first groove 51 of the first slider 5.

The mechanism further includes a first biasing member located under the third slider 7 and applying an upward biasing force to the third slider 7. In the embodiment, the first biasing component is a first compression spring 74. In the initial state, the third slider 7 is kept in an initial position by the first compression spring 74; when the ledge 23 presses the third slider 7 downwards, the third slider 7 moves downwards to deform the first compression spring 74.

Furthermore, the mechanism further includes a second biasing member located between an inner wall of the accommodating groove 71 and an upper surface of the second slider 6. The second biasing member applies a downward biasing force to the second slider 6. In the embodiment, the second biasing member is a second compression spring 75. When the third slider 7 moves downwards and drives the second slider 6 to move downwards until the boss 61 enters the first groove 51, the second slider 6 has an upward movement trend relative to the third slider 7 and presses the second compression spring 75 upwards to deform.

As shown in FIGS. 8 and 9, a distal side surface of the ledge 23 is a first inclined surface 24 of the ledge 23, which is inclined upwards from a proximal side to a distal side thereof. A proximal side surface of the third slider 7 is a first inclined surface 72 of the third slider 7, which cooperates with the first inclined surface 24 of the ledge 23. With the mutual guidance between the first inclined surface 24 of the ledge 23 and the first inclined surface 72 of the third slider 7, the ledge 23 can contact and press the third slider 7 more smoothly when moving distally.

As shown in FIGS. 9 and 10, a distal side surface of the first slider 5 is a first inclined surface 53 of the first slider 5, which is inclined upwards from a distal side to a proximal side thereof, i.e., inclined downwards from a proximal end to a distal end thereof. A proximal side surface of the boss 61 of the second slider 6 is an inclined surface 62 of the second slider 6, which cooperates with the first inclined surface 53 of the first slider 5. With the mutual guidance between the first inclined surface 53 of the first slider 5 and the inclined surface 62 of the second slider 6, the boss 61 can enter the first groove 51 more smoothly. Furthermore, the first groove 51 has a shape adapted to the shape of the first boss 61, and a proximal side surface of the first groove 51 is a second inclined surface 54 of the first slider 5, which is inclined from a distal side to a proximal side thereof.

The distal side surface of the first groove 51 is a first blocking surface 55, and a distal side surface of the boss 61 of the second slider 6 is a second blocking surface 63. The first blocking surface 55 and the second blocking surface 63 are both vertical surfaces. The first blocking surface 55 and the second blocking surface 63 are arranged with an interval therebetween when they are in their initial positions. With the cooperation between the first blocking surface 55 and the second blocking surface 63, the boss 61 prevents the first slider 5 from moving proximally when the boss 61 is inserted in the first groove 51.

After the head assembly is closed, the state of the stapler is shown in FIGS. 6-10. At this time, if the firing handle 3 is actuated to rotate for a second time, the claw 31 contacts and pushes the rack 22 to move distally. The actuating rod 2 is provided with a firing member 27, which can fire the stapler to suture and cut tissues when moving distally. During the firing process of the stapler, under the pressure from the ledge 23, the boss 61 of the third slider 6 is kept in the first groove 51 of the first slider 5, therefore the closure stability of the head assembly during the firing process of the stapler is improved.

After the stapler being fired, if the head assembly needs to be opened to separate the cartridge and the anvil, the locking member needs to be separated from the first slider 5. That is, in the embodiment, the boss 61 of the second slider 6 needs to be separated from the first groove 51 of the first slider 5.

In the embodiment, the actuating rod 2 further includes an avoiding portion. After the stapler being fired, the avoiding portion moves to be above the locking member, allowing the locking member to move upwards and at least a part of the locking member enters the avoiding portion. Therefore, the locking member is separated from the first slider 5, and the first slider 5 is free to move proximally, and the pulling sheet 12 can move distally to open the head assembly automatically.

FIGS. 11-14 show the structures of the stapler and the closure driving mechanism after the stapler being fired. In the embodiment, the avoiding portion is an avoiding groove 26 recessed upwards and located on a proximal end of the ledge 23. The avoiding groove 26 leaves a space for the upward movement of the third slider 7. In the embodiment, the first compression spring 74 is deformed by the third slider 7 during the firing process of the stapler. After the stapler being fired, as the ledge 23 no longer presses the third slider 7, the third slider 7 moves upwards under the return force of the first compression spring 74, thereby moving the boss 61 of the second slider 6 upwards to separate from the first groove 51 of the first slider 5.

In the embodiment, a distal side surface of the avoiding groove 26 is a second inclined surface 25 of the ledge 23, which inclines upwards from a distal side to a proximal side thereof. A distal side surface of the third slider 7 is a second inclined surface 73 of the third slider 7, which cooperates with the second inclined surface 25 of the ledge 23. With the mutual guidance between the second inclined surface 25 of the ledge 23 and the second inclined surface 73 of the third slider 7, the third slider 7 can get free from the pressure of the ledge 23 and enter the avoiding groove 26 more smoothly after the stapler being fired. In alternative embodiments, the second inclined surface 25 of the ledge 23 still presses the second inclined surface 73 of the third slider 7 with a smaller pressure, that is, the pressure from the pressing portion to the locking member is decreased instead of eliminated, as long as the third slider 7 can move upwards for a distance to separate the boss 61 of the second slider 6 from the first groove 51 of the first slider 5.

In alternative embodiments, the length of the ledge 23 is set according to the moving distance of the actuating rod 2 during the firing process of the stapler. The avoiding portion is formed between a proximal end portion of the ledge 23 and the actuating rod 2. Therefore, after the stapler being fired, the ledge 23 is moved to a distal side of the third slider 7, so that the third slider 7 is no longer pressed by the ledge 23. The third slider 7 moves upwards until the boss 61 of the second slider 6 is separated from the first groove 51 of the first slider 5. In the embodiment, the proximal side surface of the ledge 23 is a second inclined surface 25 of the ledge 23, which is inclined upwards from a distal side to a proximal side thereof, to realize mutual guidance with the second inclined surface 73 of the third slider 7.

FIGS. 15 and 16 show the structures of the closure driving mechanism according to the second embodiment of the present disclosure. In the embodiment, a first groove 51 is provided on an upper surface of the first slider 5, and the locking member includes an elastic sheet 9. The elastic sheet 9 includes a fixed end 91 and a movable end 92. The fixed end 91 is located at a distal side of the movable end 92 and fixed to the housing 13 of the stapler. The movable end 92 bends downwards and distally, to form a cooperation portion which is cooperated with the first groove 51 of the first slider 5.

In the initial state, the first slider 5 and the pressing portion of the actuating rod 2 are both located at a proximal side of the elastic sheet 9. When the firing handle 3 is actuated in the initial state, the firing handle 3 drives the first slider 5 to move distally to be under the cooperation portion of the elastic sheet 9. Simultaneously, the pressing portion of the actuating rod 2 moves distally until the pressing portion contacts the elastic sheet 9, the pressing portion presses the elastic sheet 9 downwards, so that at least a part of the cooperation portion enters the first groove 51 of the first slider 5 and the elastic sheet 9 is elastically deformed. The elastic sheet 9 can be made by a thin metal sheet or other materials.

After the stapler being fired, at least a part of the cooperation portion of the elastic sheet 9 enters the avoiding portion of the actuating rod 2, to decrease or eliminate the pressure from the pressing portion to the elastic sheet 9. Therefore, the elastic sheet 9 bounces upwards under the return force of the elastic sheet 9, so that the cooperation portion is separated from the first groove 51 of the first slider 5 to open the head assembly automatically.

In the embodiment, as shown in FIGS. 15 and 16, the elastic sheet 9 is further provided with a through slot 93, through which the rope 81 passes. A proximal side surface on an upper portion of the elastic sheet 9 forms a first inclined surface 94 of the elastic sheet 9. Therefore, after the pressing portion comes into contact with the elastic sheet 9, the pressing portion can continue to move distally and press the upper portion of the elastic sheet 9 more smoothly. A distal side surface of the upper portion of the elastic sheet 9 is a second inclined surface 95 of the elastic sheet 9, so that the pressing portion can be separated from the elastic sheet 9 more smoothly after the stapler being fired. A proximal side surface of the lower portion of the elastic sheet 9 forms a third inclined surface 96 of the elastic sheet 9, so that the cooperation portion of the elastic sheet 9 can enter the first groove 51 of the first slider 5 more smoothly during the closing process of the head assembly. The movable end 92 of the elastic sheet 9 is a vertical surface cooperated with a distal side surface of the first groove 51, to ensure that the elastic sheet 9 won't be accidentally separated from the first groove 51.

The closure driving mechanism and the surgical stapler have the following advantages.

The present disclosure provides a closure driving mechanism for a surgical stapler. Before the stapler is fired, and after the head assembly is closed by a closure driver, the position of the closure driver is locked by fitting cooperation between the locking member and the first slider, thereby avoiding the pulling sheet moving distally during the firing process. After the stapler being fired, the locking member moves upwards to get out of the first slider, and no longer locks the position of the closure driver, the closure driver can return to its initial position, to open the cartridge and the anvil automatically. The operation steps are simplified for the operator and the cutter can be pulled back smoothly.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A closure driving mechanism used for a surgical stapler, wherein the mechanism comprises a firing handle, a first slider, a locking member, a closure driver, and an actuating rod, wherein the actuating rod is provided with a pressing portion and an avoiding portion, wherein the avoiding portion is located on a proximal end of the pressing portion, wherein in an initial state, the pressing portion, the avoiding portion and at least a part of the first slider are all located at a proximal side of the locking member, wherein stapler comprises a pulling sheet;

when the firing handle is actuated in the initial state, the first slider is moved distally by the firing handle until the first slider is under the locking member, thereby the first slider moves the closure driver to drive the pulling sheet to move proximally, wherein the firing handle drives the actuation rod to move the pressing portion distally, then the pressing portion contacts and presses the locking member downwards to fit with the first slider;

after the stapler being fired, the pressing portion is moved to a distal side of the locking member, and the avoiding portion is moved to be above the locking member, allowing the locking member to move upwards and at least partially enter the avoiding portion, to separate from the first slider.

2. The closure driving mechanism of claim 1, wherein an upper surface of the first slider is provided with a groove, in the initial state, wherein the groove is located at the proximal side of the locking member, and wherein when the firing handle is actuated in the initial state, at least a part of the locking member enters the groove of the first slider; or the locking member is provided with a groove recessed upwards, when the firing handle is actuated in the initial state, at least a part of the first slider enters the groove of the locking member.

3. The closure driving mechanism of claim 1, wherein the pressing portion is a ledge located on a distal side of the actuating rod, and the avoiding portion is recessed upwards relative to the ledge.

4. The closure driving mechanism of claim 3, wherein a distal side surface of the ledge is a first inclined surface of the ledge, which is inclined upwards from a proximal side to a distal side thereof, and wherein a proximal side surface of the locking member is a first inclined surface of the locking member, which cooperates with the first inclined surface of the ledge.

5. The closure driving mechanism of claim 3, wherein the avoiding portion is an avoiding groove formed on the ledge.

6. The closure driving mechanism of claim 5, wherein a distal side surface of the avoiding groove is a second inclined surface of the ledge, which is inclined upwards from a distal side to a proximal side thereof, and wherein a distal side surface of the locking member is a second inclined surface of the locking member, which cooperates with the second inclined surface of the ledge.

7. The closure driving mechanism of claim 3, wherein the avoiding portion is located between a proximal side of the ledge and the actuating rod.

8. The closure driving mechanism of claim 7, wherein a proximal side surface of the ledge is a second inclined surface of the ledge, which is inclined upwards from a distal side to a proximal side thereof, and wherein a distal side surface of the locking member is a second inclined surface of the locking member, which cooperates with the second inclined surface of the ledge.

9. The closure driving mechanism of claim 1, wherein an upper surface of the first slider is provided with a groove, wherein the locking member comprises a second slider and a third slider, wherein the third slider is provided with an accommodating groove housing the second slider, and a boss is provided on a side of the second slider, wherein when the firing handle is actuated in the initial state, and wherein the boss of the second slider moves downwards and at least partially enters the groove of the first slider.

10. The closure driving mechanism of claim 9, wherein a first biasing member is provided under the third slider, and applies an upward biasing force to the third slider.

11. The closure driving mechanism of claim 1, wherein an upper surface of the first slider is provided with a groove, wherein the locking member comprises an elastic sheet having a movable end and a fixed end at a distal side of the movable end, wherein the movable end is provided with a cooperation portion cooperated with the groove of the first slider, and wherein at least a part of the cooperation portion enters the groove of the first slider when the pressing portion presses the elastic sheet.

12. The closure driving mechanism according to claim 1, wherein the first slider is connected to the closure driver through a turning assembly, which transforms the distal movement of the first slider to a proximal movement of the closure driver.

13. The closure driving mechanism according to claim 1, wherein the turning assembly comprises a pulley and a rope, wherein the pulley is located at a proximal side of the first slider, wherein the rope is arranged outside the pully, and wherein the rope is connected between the first slider and the closure driver.

14. A surgical stapler comprising the closure driving mechanism according to claim 1.

* * * * *